US012035998B2

United States Patent
Rephaeli et al.

(10) Patent No.: US 12,035,998 B2
(45) Date of Patent: Jul. 16, 2024

(54) ENDOSCOPIC SYSTEMS INCLUDING A MULTIMODE OPTICAL FIBER AND A MACHINE LEARNING CLASSIFIER FOR INTERROGATING A PORTION OF A BODY

(71) Applicant: Verily Life Sciences LLC, South San Francisco, CA (US)

(72) Inventors: Eden Rephaeli, Oakland, CA (US); Dimitri Azar, San Francisco, CA (US); James Polans, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 517 days.

(21) Appl. No.: 16/690,634

(22) Filed: Nov. 21, 2019

(65) Prior Publication Data
US 2020/0170483 A1    Jun. 4, 2020

Related U.S. Application Data

(60) Provisional application No. 62/773,352, filed on Nov. 30, 2018.

(51) Int. Cl.
*A61B 5/00* (2006.01)
*A61B 1/00* (2006.01)
(Continued)

(52) U.S. Cl.
CPC ........ *A61B 5/0084* (2013.01); *A61B 1/00006* (2013.01); *A61B 1/000096* (2022.02);
(Continued)

(58) Field of Classification Search
CPC .................... A61B 1/000095; A61B 1/000096
See application file for complete search history.

(56) References Cited

U.S. PATENT DOCUMENTS

| 5,660,181 A * | 8/1997 | Ho ..................... A61B 1/00194 600/408 |
| 7,231,243 B2 * | 6/2007 | Tearney ............. A61B 1/00082 600/407 |

(Continued)

FOREIGN PATENT DOCUMENTS

| WO | 9945838 A1 | 9/1999 |
| WO | 2007084849 A1 | 7/2007 |

OTHER PUBLICATIONS

Borhani, Navid et al., "Learning to see through multimode fibers," Optica, 5(8):960-966, Aug. 2018. (13 pages).
(Continued)

*Primary Examiner* — Joel Lamprecht
*Assistant Examiner* — Gabriel Victor Popescu
(74) *Attorney, Agent, or Firm* — Christensen O'Connor Johnson Kindness PLLC

(57) ABSTRACT

Endoscopic systems including multimode optical fibers for and methods of interrogating a portion of a body are described. In an example, the endoscopic system includes a multimode optical fiber, a coherent light source positioned to emit coherent light through the multimode optical fiber, and a photodetector positioned to absorb scattered coherent light emitted from the multimode optical fiber and configured to generate a speckled light signal based on the scattered coherent light. In an example, the endoscopic system includes a controller configured to analyze the speckled light signal with machine learning classifier and to generate an identification signal indicative of a characteristic of the portion of the body.

21 Claims, 5 Drawing Sheets

(51) Int. Cl.
*A61B 1/04* (2006.01)
*A61B 1/06* (2006.01)
*A61B 1/07* (2006.01)

(52) U.S. Cl.
CPC ...... *A61B 1/00117* (2013.01); *A61B 1/00165* (2013.01); *A61B 1/0017* (2013.01); *A61B 1/00172* (2013.01); *A61B 1/042* (2013.01); *A61B 1/0623* (2013.01); *A61B 1/0638* (2013.01); *A61B 1/0655* (2022.02); *A61B 1/0669* (2013.01); *A61B 1/07* (2013.01); *A61B 5/0066* (2013.01)

(56) References Cited

U.S. PATENT DOCUMENTS

| | | | |
|---|---|---|---|
| 8,423,110 B2* | 4/2013 | Barbato | A61B 1/0684 600/342 |
| 2008/0058629 A1* | 3/2008 | Seibel | A61B 1/044 600/368 |
| 2012/0162438 A1* | 6/2012 | Thakor | A61B 5/0035 348/161 |
| 2013/0060087 A1* | 3/2013 | Yoshida | A61B 1/07 600/112 |
| 2015/0015879 A1 | 1/2015 | Papadopoulos et al. | |
| 2017/0007187 A1 | 1/2017 | Breneisen et al. | |
| 2018/0177388 A1* | 6/2018 | Talbert | A61B 1/00096 |
| 2018/0214025 A1* | 8/2018 | Homyk | A61B 5/0082 |
| 2018/0247153 A1* | 8/2018 | Ganapati | A61B 5/0059 |
| 2018/0253839 A1* | 9/2018 | Zur | A61B 1/000095 |

OTHER PUBLICATIONS

Rahmani, Babak et al., "Multimode optical fiber transmission with a deep learning network," Light: Science & Applications, 7(69), 2018. (11 pages).

The Optical Society, "Machine learning technique reconstructs images passing through a multimode fiber," Science Daily, Aug. 9, 2018, retrieved from https://www.sciencedaily.com/releases/2018/08/180809175150.htm on Nov. 20, 2019. (3 pages).

Borhani et al., "Learning to see through multimode fibers" Arxiv, Org., Cornell University Library, May 15, 2018, 14 pages.

Rahmani et al., "Multimode optical fiber transmission with a deep learning network", Light: Science & Applications, vol. 7, No. 1, Oct. 3, 2018, 12 pages.

Turtaev, et al., "High-Fidelity multimode fibre-based endoscopy for deep-brain in vivo imaging", Arxiv, Org., Cornell University Library, Jun. 4, 2018, 10 pages.

Choi et al., "Scanner-free and Wide-Field Endoscopic Imaging by using a single multimode optical fiber", Physical Review Letters, vol. 1, No. 20, Nov. 12, 2012, 6 pages.

International Search Report and Written Opinion, mailed Mar. 16, 2020, in corresponding International Patent Application No. PCT/US2019/062687, 14 pages.

* cited by examiner

ENDOSCOPIC SYSTEMS INCLUDING A MULTIMODE OPTICAL FIBER AND A MACHINE LEARNING CLASSIFIER FOR INTERROGATING A PORTION OF A BODY

CROSS-REFERENCE TO RELATED APPLICATION

This application claims the benefit of U.S. Provisional Application No. 62/773,352, filed Nov. 30, 2018, which is hereby incorporated by reference in its entirety.

TECHNICAL FIELD

This disclosure relates generally to systems for interrogating a portion of a body, and, in particular but not exclusively, relates to endoscopic systems for interrogating a portion of a body.

BACKGROUND INFORMATION

Recognition of complex tissues and textures on or inside a body is involved in many medical procedures, such as in endoscopic procedures. Such recognition may inform decisions of what tissues to treat and how. Such recognition may be accomplished by, for example, imaging a tissue with a pixel array, thus capturing detailed spatial information. Such imaging typically includes the use of processing algorithms to recognize objects in the imaged scene. Devices for performing such imaging typically have a relatively large physical size and attendant weight due to a size of optics in the devices used to achieve minimal spatial resolution, or due to the size of a pixel array or image sensor placed adjacent to imaged tissues.

Multimode optical fibers present many advantages for light transmission, such as a large fiber core and a large numerical aperture, which generally lead to a high fiber coupling efficiency and high light gathering features. However, light propagation through a multimode optical fiber produces a speckle pattern and thus a specific spatial excitation/illumination through a multimode optical fiber is a challenge. As an optical field is coupled into the multimode optical fiber, it excites different fiber modes, which propagate along the multimode optical fiber, possibly exchanging energy between them and finally reaching an output fiber surface where they interfere generating a seemingly random speckle pattern. In addition to this modal spatial scrambling, dispersion effects in multimode optical fibers result in a temporal spreading of an input light pulse. Such challenges have limited the use of multimode optical fibers for light transmission, and particularly for fiber-based imaging.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of an endoscopic system and method for interrogating a portion of a body with a multimode optical fiber and a machine learning classifier are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 4B:
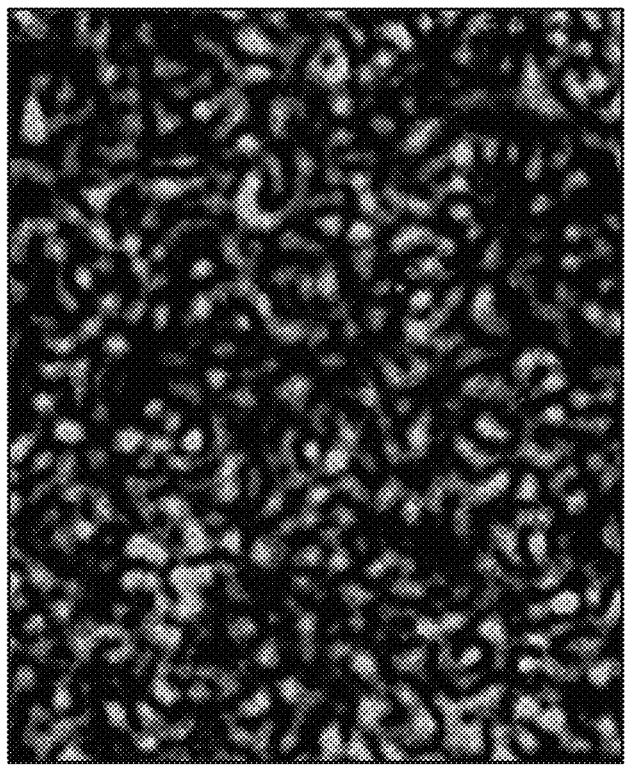
FIG. 4B is an image of a speckle pattern obtained by endoscopic systems, in accordance with an embodiment of the disclosure.
Figure 4A:
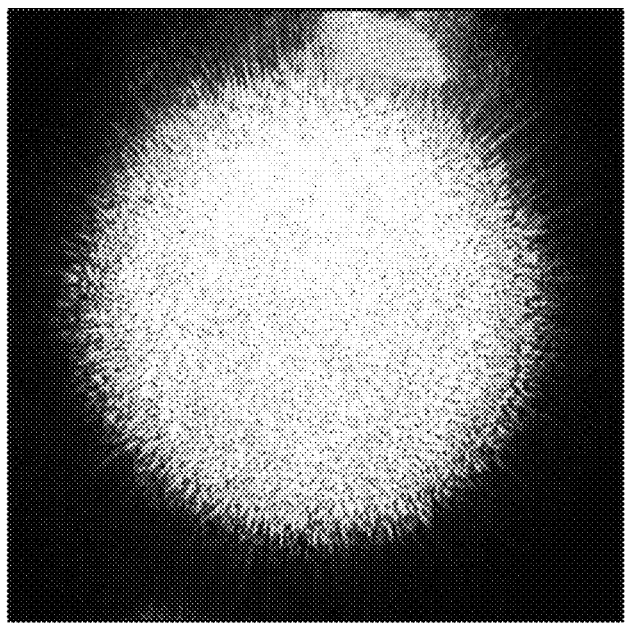
FIG. 4A is an image of a speckle pattern obtained by endoscopic systems, in accordance with an embodiment of the disclosure.

In one aspect the present disclosure provides an endoscopic system for interrogating a portion of a body. The endoscopic system of the present disclosure includes a multimode optical fiber and a coherent light source positioned to illuminate the portion of the body with coherent light. As discussed further herein, scattered coherent light received through the multimode optical fiber by a photodetector or other imaging element generally produces a pattern of dark and light spots, frequently known as a "speckle pattern" or "speckle." See for example, FIGS. 4A and 4B, which are images of speckle patterns obtained by endoscopic systems, in accordance with an embodiment of the disclosure. Such a speckle pattern is generally difficult to correlate to a portion of the body off which the coherent light is scattered or a particular characteristic thereof. Accordingly, in an embodiment, the endoscopic systems of the present disclosure include a controller including logic that, when executed by the controller, causes the endoscopic system to perform operations including analyzing the speckled light signal with a machine learning classifier to identify a characteristic of the portion of the body.

Figure 1:
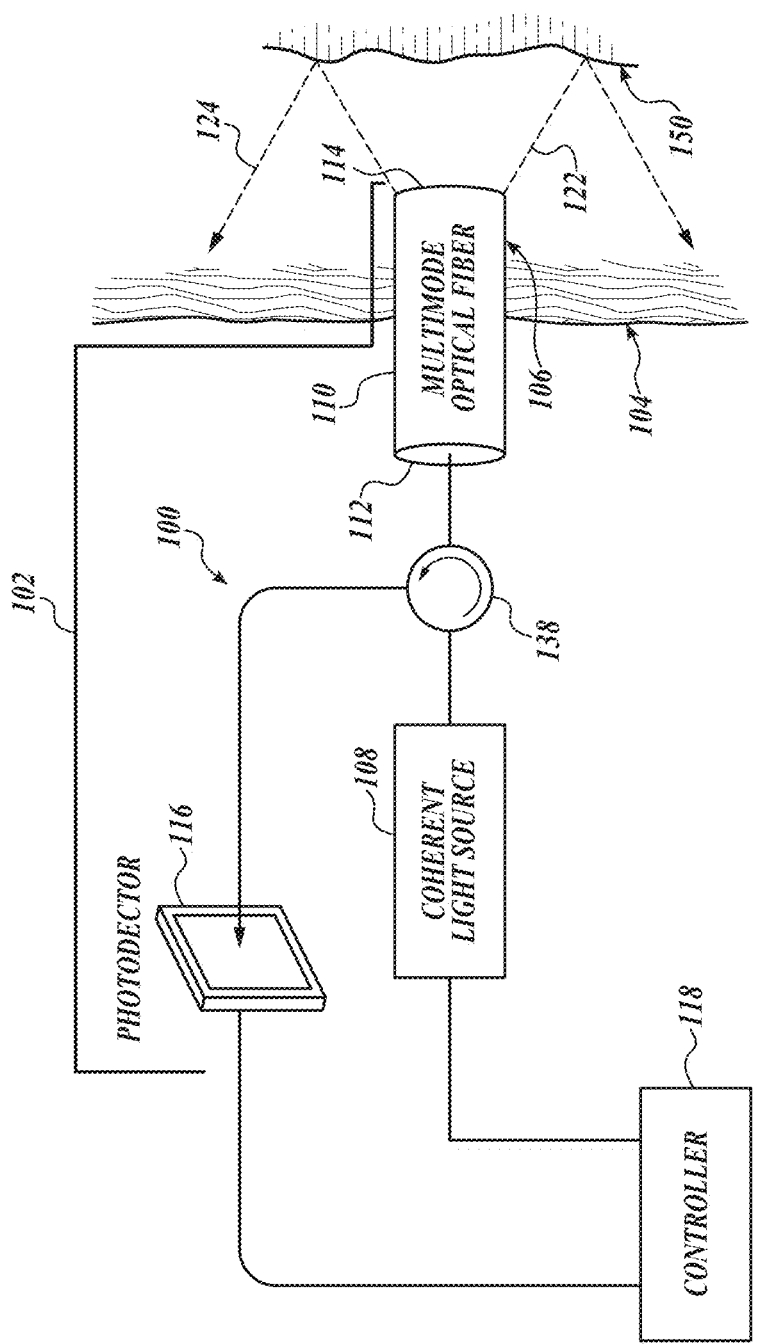
FIG. 1 is a schematic diagram of an endoscopic system, in accordance with an embodiment of the disclosure.

FIG. 1 is a schematic diagram of an endoscopic system 100, in accordance with an embodiment of the disclosure. Endoscopic system 100 is shown to include an endoscopic optical interrogator 102 and a controller 118 operatively coupled to the endoscopic optical interrogator 102.

In the illustrated embodiment, the endoscopic optical interrogator 102 includes a coherent light source 108 for emitting coherent light 122, a multimode optical fiber 110, and a photodetector 116. The coherent light source 108 can be any coherent light source 108 configured to emit coherent light 122. In an embodiment, the coherent light source 108 is chosen from a laser, a light-emitting diode, and a tungsten filament light. In an embodiment, the coherent light source 108 is configured to emit coherent light 122 having wavelengths, for example, in the ultraviolet range (10 nm-400 nm), visible range (400 nm-700 nm), near-infrared range (700 nm-1,110 nm), the infrared range (700 nm-1 mm), or combinations thereof. As shown, the multimode optical fiber 110 is positioned at a proximal end 112 to receive the coherent light 122 and shaped to emit the coherent light 122 from a distal end 114. As a portion 106 of the endoscopic optical interrogator 102 is placed in or adjacent to a portion 150 of a body 104, coherent light 122 from the coherent light source 108 is emitted onto the portion 150 of the body 104 from the distal end 114 of the multimode optical fiber 110. In this regard, coherent light 122 may be directed to portions of the body 104, for example, by directing the distal end 114 of the multimode optical fiber 110.

The distal end 114 of the multimode optical fiber 110 is further shaped to collect scattered coherent light 124 scattered off of the portion 150 of the body 104. Such scattered coherent light 124 may travel from the distal end 114 of the multimode optical fiber 110 through the multimode optical fiber 110 to the proximal end 112 of the multimode optical fiber 110 through wavelength division multiplexer 138 and to photodetector 116. As shown, the photodetector 116 is positioned to receive the scattered coherent light 124 from the proximal end 112 of the multimode optical fiber 110. By receiving the scattered coherent light 124, such as by absorption, the photodetector 116 can generate a scattered light signal based on the received scattered coherent light 124. In an embodiment the controller 118 includes logic that, when executed by the controller 118, causes the endoscopic system 100 to perform operations including emitting the coherent light 122 with the coherent light source 108; and generating a speckled light signal with the photodetector 116, wherein the speckled light signal is based on the scattered light collected at the distal end 114 of the multimode optical fiber 110.

As discussed further herein, such a speckled light signal is generally difficult to correlate to a characteristic of the portion 150 of the body 104 off of which the coherent light 122 is scattered. In that regard, in an embodiment, the controller 118 further includes logic that, when executed by the controller 118, causes the endoscopic system 100 to perform operations including analyzing the speckled light signal with a machine learning classifier to identify a characteristic of the portion of the body. In an embodiment, the machine learning classifier is configured to generate an identification signal indicative of a characteristic of the portion 150 of the body 104 based on the speckled light signal.

The machine learning classifier can include any machine learning classifier configured to generate an identification signal indicative of a characteristic of the portion 150 of the body 104 based on a speckled light signal generated by endoscopic system 100. In an embodiment, machine learning classifier includes a machine learning classifier selected from the group consisting of a support vector machine (SVM), an artificial neural network, a Bayesian network, a random forest approach, a convolutional neural network, a deep neural network, and combinations thereof. In an embodiment, the machine learning classifier is an SVM having a non-linear basis kernel.

Figure 5:
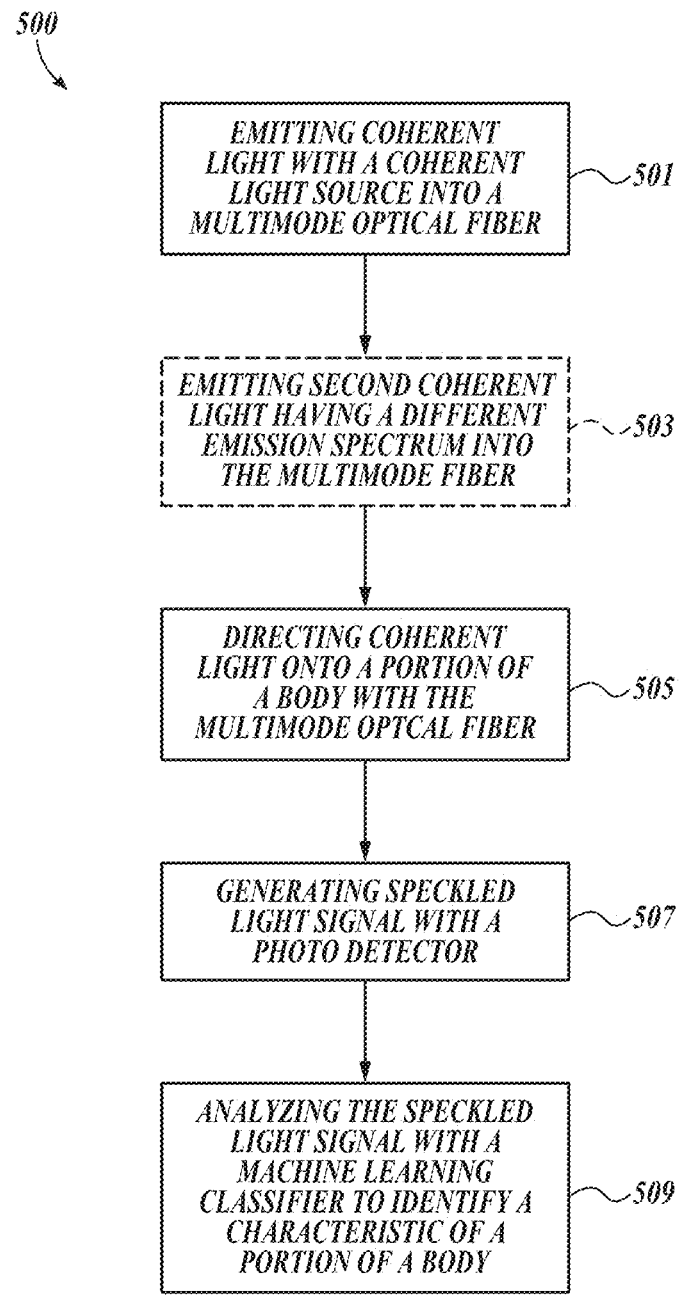
FIG. 5 is a block diagram of a method of interrogating a portion of a body, in accordance with an embodiment of the disclosure.

As discussed further herein with respect to the methods of the present disclosure, such as method 500, and with respect to FIG. 5, such a machine learning classifier may be generated by a process including generating a training data set including control speckled light signal and classifying data associated with the control speckled light signal. In an embodiment, the machine learning classifier is trained on the speckled light signal. Such a training data set may be used to correlate speckled light signal with particular characteristics of the portion 150 of the body 104. In an embodiment, the process of generating the training data set includes emitting control coherent light from a control coherent light source into a proximal end of a multimode optical fiber; directing the control coherent light onto an anatomical scene with a distal end of the multimode optical fiber; generating, with a photodetector, a control speckled light signal based on light scattered off of the anatomical scene and collected through the distal end of the multimode optical fiber; and appending classifying data to the control speckled light signal indicative of one or more characteristics of the anatomical scene. In an embodiment, generating the training data set includes generating the training data set with the endoscopic system 100.

By appending classifying data to the control speckled light signal that is indicative of one or more characteristics of the anatomical scene, the machine learning classifier can associate such one or more characteristics with the control speckled light signal. Likewise, in an embodiment, the machine learning classifier is configured to generate the identification signal based on a correlation or other comparison between one or more control speckled light signals and the speckled light signal.

Appending classifying data can include noting a texture of the anatomical scene, an absorbance spectrum of the anatomical scene, a presence of one or more tissue types in the anatomical scene, an absence of one or more tissue types in the anatomical scene, and combinations thereof. In this regard, in an embodiment, the characteristic of the portion 150 of the body 104 is selected from the group consisting of a texture of the portion 150 of the body 104, an absorbance spectrum of the portion 150 of the body 104, an emission spectrum of the portion 150 of the body 104, a presence of one or more tissue types in the portion 150 of the body 104, an absence of one or more tissue types in the portion 150 of the body 104, and combinations thereof.

In an embodiment, and as shown, the endoscopic system 100 does not include a refractive optical element, such as a lens, disposed adjacent to the distal end 114 of the multimode optical fiber 110. Such refractive optical elements may be used to collect or orient coherent light 122 from the distal end 114 of the multimode optical fiber 110 to various portions of the body 104. However, since speckled light signals are based upon coherent light 122 scattered off of the portion 150 of the body 104 and collected by the distal end 114 of the end of the multimode optical fiber 110, such refractive optical elements may not be necessary and, in an embodiment, are not included. Further, by reducing components disposed in the portion 106 of the endoscopic optical interrogator 102 shaped to enter the body 104, weight of this portion 106 of the endoscopic system 100 may be reduced, making handling and directing the portion 106 easier. Additionally, with fewer components in the portion 106 of the endoscopic optical interrogator 102 shaped to enter the body 104, the portion 106 may be removable from the endoscopic optical interrogator 102 and, in certain embodiments, sterilizable, such as by autoclaving, to be recoupled to the endoscopic optical interrogator 102 and reused in subsequent procedures. The portion 106 of the endoscopic optical interrogator 102 may have a smaller diameter and, thus, be configured to safely interrogate portions 150 of the body 104 accessed, for example, by narrow apertures. Accordingly, in an embodiment, the portion 106 of the endoscopic system 100 shaped to enter a portion 150 of a body 104 includes only the multimode optical fiber 110.

In an embodiment, the endoscopic system of the present disclosure is configured to emit coherent light from two or more coherent light sources onto the portion of the body. Such the endoscopic systems may be configured to interrogate the portion of the body with coherent light having, for example, different wavelengths and/or different coherent light intensities.

Figure 2:
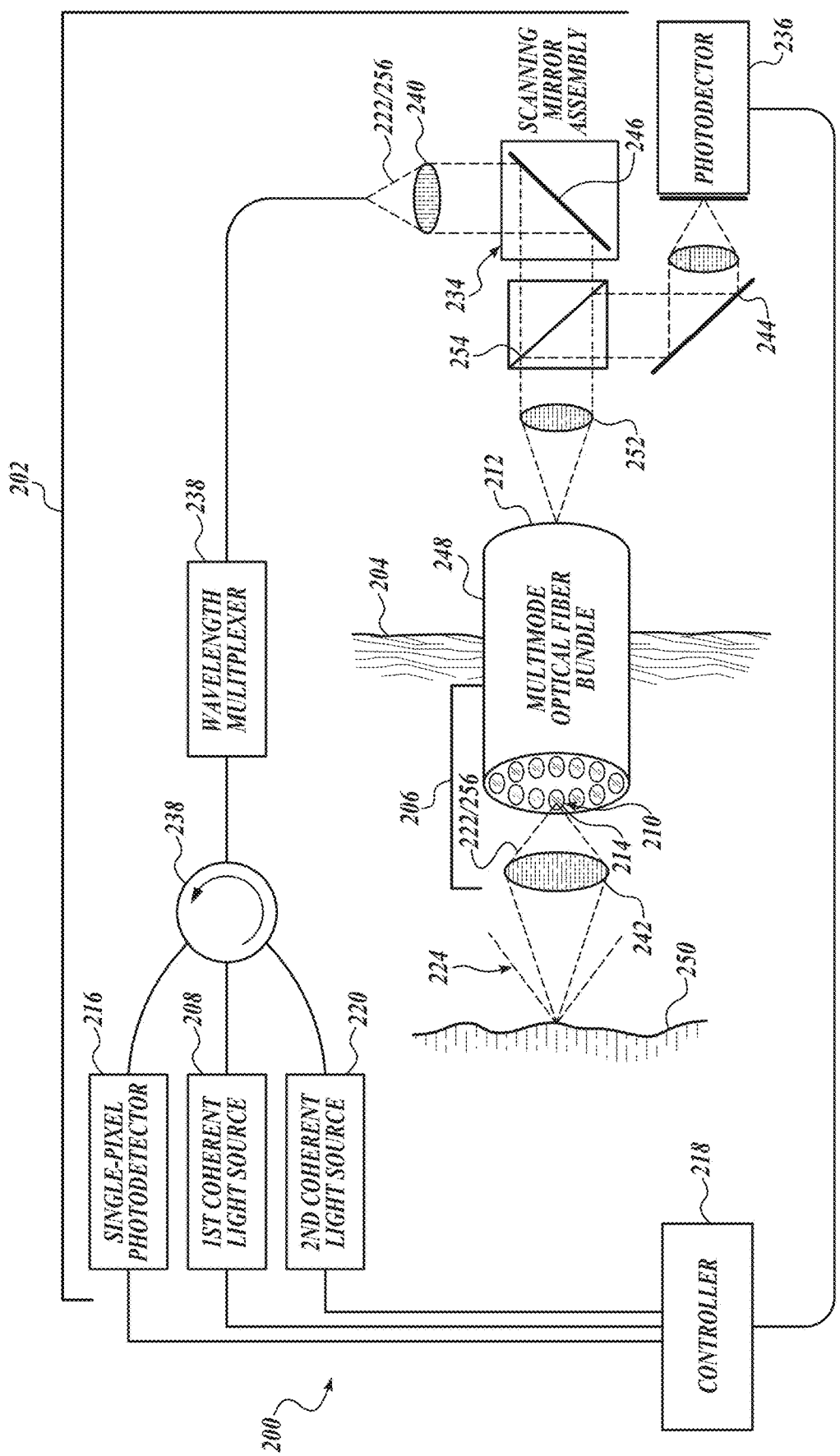
FIG. 2 is a schematic diagram of another endoscopic system, in accordance with an embodiment of the disclosure.

In that regard, attention is directed to FIG. 2 in which endoscopic system 200, in accordance with an embodiment of the disclosure, is illustrated. FIG. 2 is a schematic illustration of endoscopic system 200 including endoscopic optical interrogator 202 and controller 218. As shown, endoscopic optical interrogator 202 includes a coherent light source 208 for emitting coherent light 222; a multimode optical fiber 210 positioned at a proximal end 212 to receive the coherent light 222 and shaped to emit the coherent light 222 from a distal end 214; and a photodetector 216 positioned to receive from the proximal end 212 of the multimode optical fiber 210 scattered coherent light 224 that is scattered off the portion 250 of the body 204 and collected at the distal end 214 of the multimode optical fiber 210. A portion 206 of the endoscopic optical interrogator 202 is shaped to enter the body 204 to interrogate a portion 250 thereof.

In the illustrated embodiment, the endoscopic optical interrogator 202 includes a lens 242 shaped and positioned to focus coherent light 222 onto the portion 250 of the body 204 and to collect scattered coherent light 224 scattered off of the portion 250 the body 204 and direct the scattered coherent light 224 onto the distal end 214 of the multimode optical fiber 210. As discussed further herein with respect to FIG. 1, such a lens 242 may be optional.

In an embodiment, endoscopic system 200 includes a single multimode optical fiber (not shown, see FIG. 1). In the illustrated embodiment, multimode optical fiber 210 is one of a plurality of multimode optical fibers disposed in a multimode optical fiber bundle 248. As shown, each of the plurality of multimode optical fibers are positioned to receive coherent light 222 from the coherent light source 208 and emit the coherent light 222 onto the portion 250 of the body 204. In the illustrated embodiment, the endoscopic optical interrogator 202 includes a lens 252 shaped to focus coherent light 222 and 256 onto a proximal end 212 of multimode optical fiber 210.

Endoscopic optical interrogator 202 further includes a second coherent light source 220 for emitting second coherent light 256. As shown, coherent light source 208 and second coherent light source 220 are positioned to emit coherent light 222 and 256, respectively, into the proximal end 212 of multimode optical fiber 210. In the illustrated embodiment, endoscopic optical interrogator 202 includes wavelength division multiplexer 238 configured combine coherent light 222 and 256 emitted by coherent light source 208 and second coherent light source 220 for receipt by the proximal end 212 of the multimode optical fiber 210. As shown, the endoscopic optical interrogator 202 further includes a collimating lens 240 shaped to collimate coherent light 222.

In an embodiment, the second coherent light source 220 has an emission spectrum different than an emission spectrum of the first coherent light source 208. In this regard, the endoscopic system 200 is configured to interrogate the portion 250 of the body 204 with coherent light 222 and 256 having different wavelengths. Such coherent light 222 and 256 having different wavelengths may be suitable to interrogate different aspects of the portion 250 of the body 204. For example, in an embodiment coherent light source 208 is configured to emit coherent light 222 in the infrared and/or near-infrared range, such as coherent light 222 having a wavelength in a range of about 700 nm to about 1,100 nm, whereas second coherent light source 220 is configured to emit second coherent light 256 in the visible range, such as second coherent light 256 having a wavelength in a range of about 400 nm to about 700 nm. In this regard, the endoscopic system 200 is configured to assay, for example, perfusion of tissue 250 with blood, which absorbs light in the infrared and near-infrared range, and absorbance and/or emission of that same tissue 250 in response to visible light.

Further, by interrogating the portion 250 of the body 204 with coherent light 222 and 256 having multiple wavelength ranges, the endoscopic system 200 is configured to generate a more robust and higher-dimensional set of variables on which to train a machine learning classifier. As noted above, the endoscopic system 200 includes a controller 218. As shown the controller 218 is operatively coupled to the coherent light source 208, the second coherent light source 220, and the photodetector 216. In an embodiment, the controller 218 includes logic that, when executed by the controller 218, causes the endoscopic system 200 to perform operations including emitting the coherent light 222 and 256 with the first coherent light source 208 and the second coherent light source 220; generating a speckled light signal with the photodetector 216, the speckled light signal based on the scattered coherent light 224 collected at the distal end 214 of the multimode optical fiber 210; and analyzing, with a machine learning classifier, the speckled light signal to generate an identification signal indicative of a characteristic of the portion 250 of the body 204. By analyzing, with the machine learning classifier, the speckled light signals based on scattered coherent light 224 having, for example, two or more wavelength ranges, the scattered light signal is generally higher dimensional and more robust in generating an identification signal indicative of a characteristic of the portion 250 of the body 204. Likewise, by training the machine learning classifier on speckled light signals based on scattered coherent light 224 having two or more wavelength ranges, the identification signal may be indicative or two or more characteristics of the portion 250 of the body 204, such as the presence or absence of two or more tissue types in the portion 250 of the body 204.

As above, the endoscopic system 200 may be configured to emit coherent light 222 and 256 from the first coherent light source 208 and the second coherent light source 220 at different intensities. The absolute and relative intensities of the first coherent light source 208 and the second coherent light source 220 may be determined by a machine learning process as discussed further herein with respect to the methods of the present disclosure. Such different intensities may be suitable in certain embodiments, for example, for increasing contrast between two or more tissue types having different absorbance or scattering characteristics.

As shown, endoscopic optical interrogator 202 includes two photodetectors 216 and 236. Endoscopic optical interrogator 202 is shown to further include a semi-transmissive mirror 254 configured to reflect a portion of scattered coherent light 224 and to allow another portion of scattered coherent light 224 to pass through. Semi-transmissive mirror 254 is positioned to direct a portion of scattered coherent light 224 to first photodetector 216 and another portion to mirror 244 and second photodetector 236.

In an embodiment, photodetector 216 is configured to generate a speckled light signal based upon coherent light 222 emitted by coherent light source 208 and scattered off of the portion 250 of the body 204, and second photodetector 236 is configured to generate a speckled light signal based upon coherent light 256 emitted by second coherent light source 220 and scattered off of the portion 250 of the body 204. In this regard, first photodetector 216 and second photodetector 236 may generate different speckled light signal from light of the same wavelength.

In the illustrated embodiment, photodetector 216 is a single-pixel photodetector 216. As used herein, a single-pixel photodetector refers to a photodetector having only a single photodiode. This is in contrast to a multi-pixel array having two or more photodiode pixels, such as second photodetector 236. Such a single-pixel photodetector 216 may be suitable to generate speckled light signals based on the absorption of infrared and/or near-infrared light. Photodetectors responsive infrared and near-infrared light, such as those including indium gallium arsenide (InGaAs) photodiodes, tend to be expensive and multi-pixel InGaAs photodiode arrays are correspondingly more expensive than single-pixel InGaAs photodiodes.

As shown, endoscopic optical interrogator 202 further includes a scanning mirror assembly 234 configured to selectively direct the scattered coherent light 224. In an embodiment, the scanning mirror assembly 234 includes a micro-electromechanical system for selectively altering an orientation of a scanning mirror 246 of the scanning mirror assembly 234 to selectively direct the scattered coherent light 224.

In the illustrated embodiment, scanning mirror assembly 234 is operatively coupled to controller 218, which includes logic that, when executed by the controller 218, causes the endoscopic system 200 to perform operations including selectively directing, with the scanning mirror assembly 234, a portion of the scattered coherent light 224 collected by the distal end 214 of the multimode optical fiber 210 to the single-pixel photodetector 216. Accordingly, endoscopic optical interrogator 202 is configured to interrogate a number of portions of the portion 250 of the body 204 by, for example, sequentially selectively directing scattered coherent light 224 scattered from various portions of the body 204 to the single-pixel photodetector 216. In this regard, the endoscopic system 200 is further configured to generate speckled light signal based on the various portions of body 204. In an embodiment, selectively directing portions of the scattered coherent light 224 collected by the distal end 214 of the multimode optical fiber 210 from various portions of the body 204 to the single-pixel photodetector 216 includes selectively directing portions of the scattered coherent light 224 from various portions of the body 204, such as by rastering or otherwise systematically directing the scattered coherent light 224 scattered from various portions of the body 204 to the single-pixel photodetector 216.

In an embodiment, controller 218 includes logic that, when executed by the controller 218, causes the endoscopic system 200 to perform operations including: emitting coherent light 222 and 256 from the coherent light sources 208 and 220; generating a speckled light signal with the photodetector(s) 216 and/or 236, the speckled light signal based on the scattered coherent light 224 collected at the distal end 214 of the multimode optical fiber 210; and analyzing, with a machine learning classifier, the speckled light signal to generate an identification signal indicative of a characteristic of the portion 250 of the body 204.

As discussed further herein with respect to FIG. 1, the machine learning classifier may be generated by a process including generating a training data set, such as by appending classifying data to the control speckled light signal indicative of one or more characteristics of an anatomical scene. In an embodiment, generating the training data set includes emitting control coherent light from two or more control coherent light sources onto an anatomical scene through a multimode optical fiber, wherein the two or more control coherent light sources have different emission spectra. In that regard, speckled light signal based upon control coherent light scattered off of the anatomical scene is based on control coherent light emitted from the two or more coherent light sources having different emission spectra.

Such a machine learning classifier generated with two or more control coherent light sources having different emission spectra may be suitable to analyze speckled light signal based on scattered coherent light emitted from two or more coherent light sources and scattered off of the portion of the body, particularly where the two control coherent light sources have emission spectra corresponding to emission spectra of the two or more coherent light sources. Such a machine learning classifier may be configured to generate identification signal more indicative of a characteristic of the portion of the body because the control speckled light signals are based on scattered light having the same or similar wavelengths as the scattered coherent light on which the speckled light signal is based.

Figure 3:
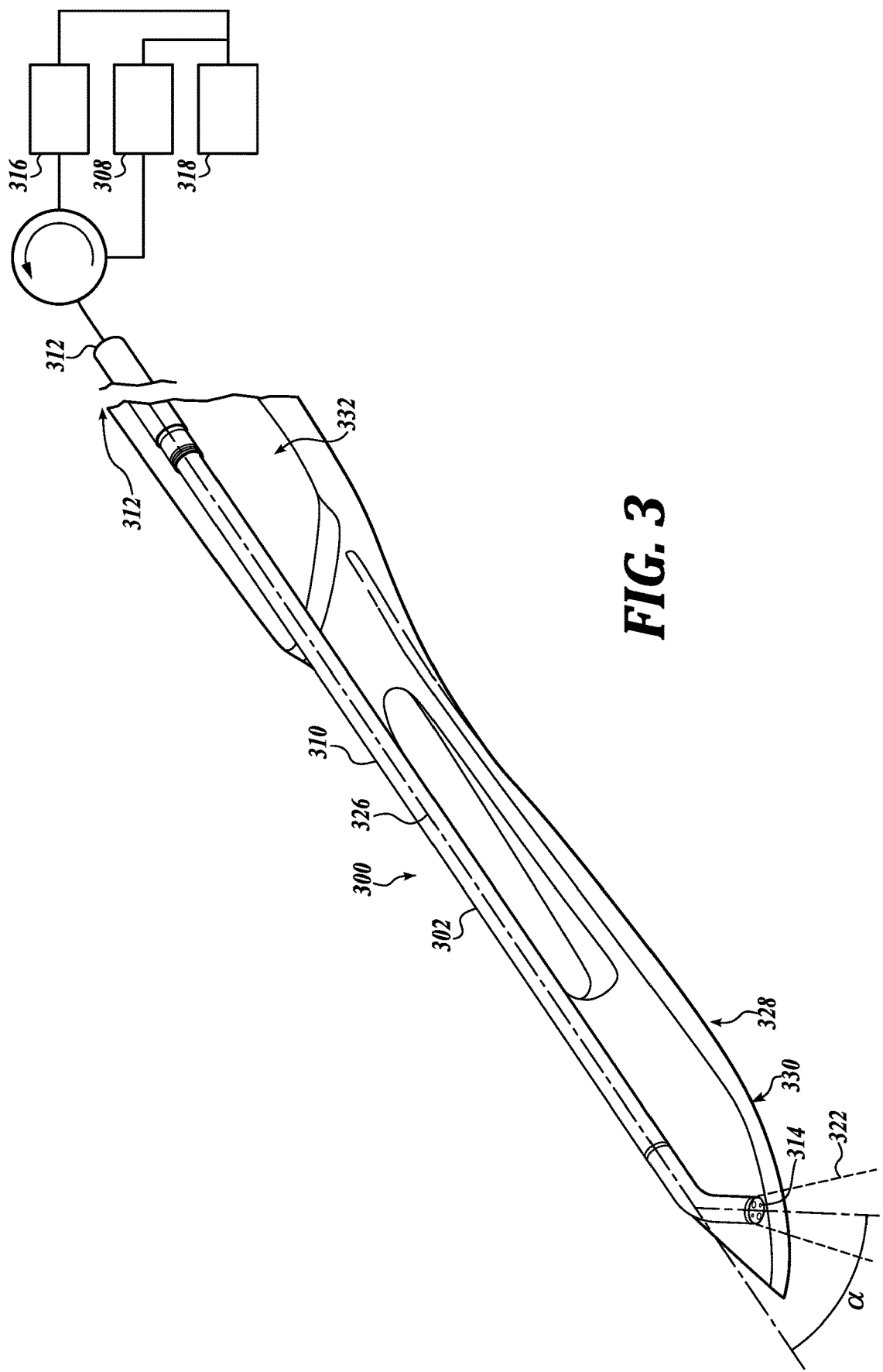
FIG. 3 an illustration of a partial perspective view of another endoscopic system including a surgical instrument, in accordance with an embodiment of the disclosure.

In an embodiment, the endoscopic system of the present disclosure includes a surgical instrument shaped to be placed adjacent to a portion of a body and coupled to a portion of the endoscopic optical interrogator. In that regard, attention is directed to FIG. 3, in which an endoscopic system 300 in accordance with an embodiment of the present disclosure is shown including a multimode optical fiber 310 coupled to a surgical instrument 328, where FIG. 3 is a partial perspective view of endoscopic system 300.

Endoscopic system 300 is shown to include an endoscopic optical interrogator 302 including a multimode optical fiber 310 coupled to a surgical instrument 328 and a controller 318. In an embodiment, the endoscopic optical interrogator 302 is an example of endoscopic optical interrogators 102 and/or 202 of endoscopic systems 100 and/or 200. In the illustrated embodiment, the surgical instrument 328 is a scalpel 328 where the multimode optical fiber 310 is shown coupled to a blade portion 330 and a handle portion 332 of the scalpel 328 with a distal end 314 of the multimode optical fiber 310 shaped to emit coherent light 322 and positioned adjacent to the blade portion 330 of the scalpel 328. By coupling the multimode optical fiber 310 to the surgical instrument 328, such as a surgical instrument 328 shaped to enter a portion of a body (not shown), the multimode optical fiber 310 can be placed inside the body and emit coherent light 322 therein. In this regard, the endoscopic system 300 can interrogate a portion of the body inside of the body as the surgical instrument 328 is placed in the portion of the body.

While a scalpel 328 is illustrated, it will be understood that other surgical instruments are also encompassed by the present disclosure. In an embodiment the surgical instrument 328 is selected from the group consisting of a scalpel, a stent, a trocar, a catheter, a lancet, a needle, a drill, and combinations thereof.

In an embodiment, the multimode optical fiber 310 is shaped to be removably coupled to the surgical instrument 328. In this regard, the surgical instrument 328 can be placed inside the body and removed leaving the multimode optical fiber 310 inside the body. Likewise, the multimode optical fiber 310 can be uncoupled from the surgical instrument 328 and other components of the endoscopic system 300, such as for cleaning of the multimode optical fiber 310 after use so that it can be sterilized and reused.

Endoscopic system 300 is shown to further include a coherent light source 308 for emitting coherent light 322 into a proximal end 312 of the multimode optical fiber 310; a photodetector 316 positioned to receive from the proximal end 312 of the multimode optical fiber 310 scattered coherent light that is scattered off the portion of the body and collected at a distal end 314 of the multimode optical fiber 310; and a controller 318 operatively coupled to the coherent light source 308 and the photodetector 316. In an embodiment, endoscopic system 300 includes two or more coherent light sources (not shown) positioned to emit coherent light into a proximal end 312 of the multimode optical fiber 310, as discussed further herein with respect to FIG. 2.

As discussed further herein with respect to FIGS. 1 and 2, the controller 318 includes logic that, when executed by the controller 318, causes the endoscopic system 300 to perform operations including emitting the coherent light 322 with the coherent light source 308; generating a speckled light signal with the photodetector 316, the speckled light signal based on the scattered coherent light collected at the distal end 314 of the multimode optical fiber 310; and analyzing, with a machine learning classifier, the speckled light signal to generate an identification signal indicative of a characteristic of the portion of the body. In this regard, the endoscopic system 300 is configured to generate an identification signal based on a characteristic of the portion of the body adjacent to a distal end 314 of the surgical instrument 328.

In the illustrated embodiment, endoscopic optical interrogator 302 including the multimode optical fiber 310 has a central axis 326 extending along a portion of the multimode optical fiber 310. As shown, at a distal end 314 of the multimode optical fiber 310 bends away from the central axis 326. In this regard, a central portion of the multimode optical fiber 310 is positioned at an angle that is non-parallel to the central axis 326. Further, coherent light 322 is emitted from the distal end 314 of the multimode optical fiber 310 at an angle α that is non-parallel to the central axis 326. In an embodiment, angle α is in a range of about 1° to about 45°. In an embodiment, angle α is in a range of about 10° to about 40°. In an embodiment, angle α is about 30°. Multimode optical fiber 310 shaped to emit coherent light 322 from distal end 314 at an angle α non-parallel to central axis 326 are suitable to emit coherent light 322 onto portions of the body not directly in front of the surgical instrument 328. In this regard, endoscopic system 300 is configured to interrogate portions of the body that are, for example, not in line with an entry path of the surgical instrument 328.

As discussed further herein with respect to method 500 of FIG. 5, the machine learning classifier can be generated by generating a training data set. In an embodiment, such a training data set is generated by emitting control coherent light from a control coherent light source into a proximal end 312 of a multimode optical fiber 310; directing the control coherent light onto an anatomical scene with a distal end 314 of the multimode optical fiber 310; generating, with a photodetector 316, a control speckled light signal based on light scattered off of the anatomical scene and collected through the distal end 314 of the multimode optical fiber 310; and appending classifying data to the control speckled light signal indicative of one or more characteristics of the anatomical scene. Speckled light signals generated with the photodetector 316 generally change as an angle at which the coherent light 322 impinges on a portion of the body changes. Accordingly, in an embodiment, generating the training data includes emitting control coherent light from a multimode optical fiber onto the anatomical scene at various angles of incidence. In that regard, the endoscopic system 300 is configured to generate an identification signal indicative of a characteristic of the portion of the body where coherent light 322 is emitted from the endoscopic system 300 at various angles, such as angles non-parallel to a central axis 326 of the endoscopic optical interrogator 302.

In another aspect, the present disclosure provides a method of interrogating a portion of a body. In that regard, attention is directed to FIG. 5 in which a block diagram of a method 500 of interrogating a portion of a body, in accordance with an embodiment of the disclosure, is illustrated. In an embodiment, method 500 is an example of a method of interrogating a portion of a body with endoscopic systems 100, 200, and/or 300.

Method 500 can begin with process block 501, which includes emitting coherent light from a coherent light source into a proximal end of a multimode optical fiber. Coherent light can be emitted from any source of coherent light, such as a laser, a light-emitting diode, a tungsten filament light, and the like.

In an embodiment, the coherent light source is disposed adjacent to the proximal end of the multimode optical fiber and not, for example, adjacent to the distal end of the multimode optical fiber or other portion of the endoscopic system shaped to enter a portion of the body. In such a configuration, the portion of the endoscopic system shaped to enter the body includes fewer components and, accordingly, generally weighs less than if the coherent light source were placed in the body, making the endoscopic system easier for a user to manipulate and direct.

Process block 501 can be followed by process block 503, which includes emitting second coherent light from a second coherent light source into the proximal end of the multimode optical fiber. In an embodiment, the second coherent light source has an emission spectrum different from an emission spectrum of the coherent light source of process block 501. In an embodiment, first coherent light and second coherent light having different wavelengths travel through the multimode optical fiber. In an embodiment, process block 503 is optional. While emitting second coherent light from a second coherent light source is illustrated, it will be understood that the method can further include emitting additional coherent light from additional coherent light sources.

In an embodiment, first coherent light is emitted at a different intensity than second coherent light. As described further herein, such different emission intensities may be suitable to provide, for example, greater contrast between tissue types, textures, and the like in generating speckled light signal and identification signal. The absolute intensities and relative intensities of the first coherent light and second coherent light can be determined, for example, by a machine learning method. Such a machine learning method can include directing first and second control coherent light onto anatomical scenes from multimode optical fibers at various absolute and relative intensities to generate control coherent light signal, such as with a photodetector positioned to receive scattered coherent light, and appending classifying data thereto. Relative intensities of first and second control coherent light that generate control speckled light signal providing, for example, contrast between tissue types may be used to inform relative intensities of first coherent light and second coherent light used to generate speckled light signal.

Process blocks 501 and/or 503 can be followed by process block 505, which includes directing the coherent light onto the portion of the body with a distal end of the multimode optical fiber. In an embodiment, the portion of the body is a portion of the body inside the body. In an embodiment, the portion of the body is a portion of the body on an outer surface of the body. In an embodiment, directing the coherent light onto the portion of the body includes directing the distal end of the multimode optical fiber adjacent to the portion of the body such that coherent light emitted therefrom impinges on the portion of the body. As discussed further herein with respect to FIG. 3, the multimode optical fiber can be coupled to a surgical instrument. Accordingly, in an embodiment, directing the coherent light onto the portion of the body includes directing the surgical instrument adjacent to the portion of the body, such as by directing a scalpel, endoscope, and the like adjacent to the portion of the body.

In an embodiment, directing coherent light onto the portion of the body includes emitting coherent light from a multimode optical fiber at an angle non-parallel relative to a central axis of an endoscopic optical interrogator. As discussed further herein with respect to FIG. 3, by emitting coherent light at an angle that is other than parallel to a central axis of the endoscopic optical interrogator, the coherent light can impinge upon portions of the body not directly in front of the endoscopic optical interrogator, such as those portions of the body not in line with an entry path of the endoscopic optical interrogator.

Process block 505 can be followed by process block 507, which includes generating a speckled light signal with a photodetector. In an embodiment, the speckled light signal is based on scattered coherent light that is scattered off of the portion of the body and collected through the distal end of the multimode optical fiber. As the scattered coherent light exits the proximal end of the multimode optical fiber it impinges upon the photodetector. The photodetector can be any photodetector configured to generate a speckled light signal based on scattered coherent light scattered off of the portion of the body and collected through the distal end of the multimode optical fiber. In an embodiment, the photodetector is selected from the group consisting of a photodiode, a phototransistor, and a photovoltaic cell. As discussed further herein with respect to FIG. 2, the photodetector can include a single-pixel photodetector, such as an InGaAs single-pixel photodetector. In an embodiment, the photodetector includes a multi-pixel array. In an embodiment, the endoscopic system includes two photodetectors, as discussed further herein with respect to FIG. 2, particularly when two coherent light sources are used to interrogate the portion of the body.

In an embodiment, levels of digital or other filters of the photodetector are set and configured by a machine learning process. In an embodiment, such filters are configured to enhance contrast between, for example, tissue types. In an embodiment, the machine learning process includes generating control speckled light signal at various filter configurations to identify filter settings that enhance contrast between tissue types.

In an embodiment, the photodetector is disposed adjacent to the proximal end of the multimode optical fiber and away from the distal end of the multimode optical fiber or other portion of the endoscopic system shaped to enter a portion of the body. As discussed further herein with respect to placement of the coherent light source, by limiting components of the endoscopic system that enter the portion of the body, the portion of the endoscopic system that enters the body is easier for a user to manipulate and position. Further, in an embodiment, by reducing the components of the endoscopic system disposed in a portion of the endoscopic system shaped to enter a body, that portion may be sterilized and reused.

Process block 507 can be followed by process block 509, which includes analyzing the speckled light signal with a machine learning classifier to generate an identification signal indicative of a characteristic of the portion of the body.

The machine learning classifier can include any machine learning classifier configured to generate the identification signal based on the speckled light signal. In an embodiment, machine learning classifier includes a machine learning classifier selected from the group consisting of an SVM, an artificial neural network, a Bayesian network, a random forest approach, a convolutional neural network, a deep neural network, and combinations thereof. In an embodiment, the SVM has a non-linear basis kernel.

In an embodiment, the machine learning classifier is generated based on a training data set that includes control speckled light signal based on scattered coherent light scattered off of anatomical scenes and classifying data indicative of one or more characteristics of the anatomical scenes. By correlating classifying data indicative of the one or more characteristics of anatomical scenes with the corresponding control speckled light signals, the machine learning classifier may be configured to generate identification signals based on speckled light signals based on scattered coherent light scattered off of a portion of a body.

In an embodiment, the characteristic of the anatomical scene is selected from the group consisting of a texture of the anatomical scene, an absorbance spectrum of the anatomical scene, an emission spectrum of the anatomical scene, a presence of one or more tissue types in the anatomical scene, an absence of one or more tissue types in the anatomical scene, and combinations thereof. In that regard, the machine learning classifier may be configured to generate an identification signal indicative of a characteristic of the portion of the body, wherein the characteristic of the portion of the body is selected from the group consisting of a texture of the portion of the body, an absorbance spectrum of the portion of the body, an emission spectrum of the portion of the body, a presence of one or more tissue types in the portion of the body, an absence of one or more tissue types in the portion of the body, and combinations thereof.

In an embodiment, generating a training data set includes emitting control coherent light from a control coherent light source into a proximal end of a multimode optical fiber; directing the control coherent light onto an anatomical scene with a distal end of the multimode optical fiber; generating, with a photodetector, a control speckled light signal based on light scattered off of the anatomical scene and collected through the distal end of the multimode optical fiber; and appending classifying data to the control speckled light signal indicative of one or more characteristics of the anatomical scene. In an embodiment, generating the training data set is generated by using an endoscopic system as described herein, such an endoscopic systems 100, 200, and/or 300. In an embodiment appending classifying data includes annotating, such as by a laboratory technician, the classifying data to the control speckled light signal. In an embodiment, appending includes measuring or otherwise identifying the characteristic with a method, such as by imaging, that does not include emitting and receiving light through a multimode optical fiber.

In an embodiment, generating the training dataset further includes emitting second control coherent light from a second control coherent light source into the distal end of the multimode optical fiber, wherein the second control coherent light source has a second emission spectrum different than an emission spectrum of the control coherent light source; and directing the second control coherent light onto the anatomical scene with the distal end of the multimode optical fiber. By emitting second control coherent light, the control speckled light signal can be based upon the second control light, as well as first control coherent light. Because the second control coherent light and the first control coherent light have different wavelengths, the machine learning classifier can be based upon speckled light signals based on both the second scattered control coherent light and first scattered coherent control light. As discussed further herein, by emitting coherent light of different wavelengths onto a portion of the body, such as a portion of a body and/or anatomical scene, the speckled light signals generated therefrom have greater degrees of freedom and may be indicative of additional aspects of the portion of the body and/or anatomical scene.

Such machine learning classifiers based on control speckled light signals based upon scattered first and second control coherent light may be particularly suitable for analyzing speckled light signals based upon first and second coherent light scattered off of the portion of the body where wavelengths of first and second control coherent light correspond to wavelengths of first and second coherent light.

Speckled light signals generated with the photodetector generally change as an angle at which the coherent light impinges on a portion of the body changes. Accordingly, in an embodiment, generating the training data includes emitting control coherent light from a multimode optical fiber onto the anatomical scene at various angles of incidence. In that regard, the machine learning classifier is configured to generate an identification signal indicative of a characteristic of the portion of the body where coherent light is emitted from the endoscopic system at various angles, such as angles non-parallel to a central axis of the endoscopic optical interrogator.

The order in which some or all of the process blocks appear in each process should not be deemed limiting. Rather, one of ordinary skill in the art having the benefit of the present disclosure will understand that some of the process blocks may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An endoscopic system for interrogating a portion of a body, the system comprising:
    an endoscopic optical interrogator having a portion shaped to enter the body, the endoscopic optical interrogator comprising:
        a coherent light source for emitting coherent light;
        a multimode optical fiber bundle comprising a plurality of multimode optical fibers, wherein each multimode optical fiber of the plurality of multimode optical fibers is positioned at a proximal end to receive the coherent light and shaped to emit the coherent light from a distal end, and wherein the emitted coherent light is configured to be delivered by each of the multimode optical fibers of the plurality of multimode optical fibers in a direction out of distal ends of the multimode optical fibers; and
        a photodetector positioned to receive scattered coherent light from the proximal ends of the plurality of multimode optical fibers that is scattered off the portion of the body and collected at the distal ends of the plurality of multimode optical fibers, wherein each multimode optical fiber of the plurality of multimode optical fibers is configured to deliver scattered coherent light through the proximal ends to the photodetector; and
    a controller operatively coupled to the coherent light source and the photodetector, the controller including logic that, when executed by the controller, causes the endoscopic system to perform operations including:
        emitting the coherent light with the coherent light source into the proximal ends of and through the plurality of multimode optical fibers;
        generating a speckled light signal with the photodetector, the speckled light signal based on the scattered coherent light collected at the distal ends of the plurality of multimode optical fibers and received by the photodetector at the proximal ends; and
        analyzing the speckled light signal with a machine learning classifier to identify a characteristic of the portion of the body.

2. The endoscopic system of claim 1, wherein the coherent light source is a first coherent light source, and wherein the endoscopic optical interrogator further comprises a second coherent light source for emitting second coherent light, wherein the second coherent light source has an emission spectrum different than an emission spectrum of the first coherent light source.

3. The endoscopic system of claim 2, wherein the controller is operatively coupled to the second coherent light source and further includes logic that, when executed by the controller, causes the endoscopic system to perform operations including:
   emitting the coherent light from the first coherent light source at a first intensity; and
   emitting the second coherent light from the second coherent light source at a second intensity different than the first intensity.

4. The endoscopic system of claim 1, wherein the portion of the endoscopic optical interrogator shaped to enter the body includes the multimode optical fiber.

5. The endoscopic system of claim 1, wherein the characteristic of the portion of the body is selected from the group consisting of a texture of the portion of the body, an absorbance spectrum of the portion of the body, an emission spectrum of the portion of the body, a presence of one or more tissue types in the portion of the body, an absence of one or more tissue types in the portion of the body, and combinations thereof.

6. The endoscopic system of claim 1, wherein the endoscopic system does not include a refractive optical element disposed adjacent to the distal end of the multimode optical fiber.

7. The endoscopic system of claim 1, wherein a distal end of a multimode optical fiber of the plurality of multimode optical fibers is shaped to emit the coherent light onto the portion of the body at a non-parallel angle relative to a central axis of the endoscopic optical interrogator.

8. The endoscopic system of claim 1, wherein a multimode optical fiber of the plurality of multimode optical fibers is coupled at a distal end to a surgical instrument shaped to be placed adjacent to the portion of the body.

9. The endoscopic system of claim 8, wherein the surgical instrument is selected from the group consisting of a scalpel, a stent, a trocar, a catheter, a lancet, a needle, a drill, and combinations thereof.

10. The endoscopic system of claim 1, wherein the photodetector is a single-pixel photodetector.

11. The endoscopic system of claim 10, further comprising a scanning mirror assembly configured to selectively direct the scattered coherent light, wherein the controller is operatively coupled to the scanning mirror assembly and further includes logic that, when executed by the controller, causes the endoscopic system to perform operations including:
   selectively directing a portion of the scattered coherent light collected by the distal ends of the multimode optical fibers with the scanning mirror assembly to the single-pixel photodetector.

12. The endoscopic system of claim 1, wherein the photodetector is a first photodetector, the endoscopic optical interrogator further comprising a second photodetector positioned to receive the scattered coherent light collected at the distal ends of the plurality of multimode optical fibers from the proximal ends of the plurality of multimode optical fibers.

13. The endoscopic system of claim 12, wherein the second photodetector is configured to generate a second speckled light signal based on the scattered coherent light, wherein the second speckled light signal is different than the speckled light signal generated by the first photodetector.

14. The endoscopic system of claim 12, wherein the second photodetector includes a plurality of pixels disposed in a pixel array.

15. A non-transitory, machine-readable storage medium having instructions stored thereon, which when executed by a processing system, cause the processing system to perform a method comprising:
   emitting coherent light from a coherent light source into proximal ends of a plurality of multimode optical fibers disposed in a multimode optical fiber bundle, through the plurality of multimode optical fibers, and onto a portion of a body from distal ends of the plurality of multimode optical fibers, wherein the emitted coherent light is delivered by each multimode optical fiber of the plurality of multimode optical fibers in a direction out of the distal ends into the portion of the body;
   generating a speckled light signal with a photodetector, wherein the speckled light signal is based on scattered coherent light that is scattered off of the portion of the body and collected through the distal ends of the plurality of multimode optical fibers and received by the photodetector at the proximal ends, wherein each multimode optical fiber delivers scattered coherent light through the proximal ends to the photodetector; and
   analyzing the speckled light signal with a machine learning classifier to identify a characteristic of the portion of the body.

16. The non-transitory, machine-readable storage medium of claim 15, wherein the coherent light source is a first coherent light source and the coherent light is first coherent light, the method further comprising emitting second coherent light from a second coherent light source into the proximal end of the multimode optical fiber, wherein the second coherent light source has an emission spectrum different than an emission spectrum of the first coherent light source.

17. The non-transitory, machine-readable storage medium of claim 15, wherein the characteristic of the portion of the body is selected from the group consisting of a texture of the portion of the body, an absorbance spectrum of the portion of the body, an emission spectrum of the portion of the body, a presence of one or more tissue types, an absence of one or more tissue types, and combinations thereof.

18. The non-transitory, machine-readable storage medium of claim 15, further comprising training the machine learning classifier, wherein training the machine learning classifier comprises training the machine learning classifier on the speckled light signal to generate an identification signal indicative of a characteristic of the portion of the body.

19. The non-transitory, machine-readable storage medium of claim 15, further comprising training the machine learning classifier, wherein training the machine learning classifier comprises:
   emitting control coherent light from a control coherent light source into proximal ends of the plurality of multimode optical fibers and onto an anatomical scene with distal ends of the plurality of multimode optical fibers;
   generating a control speckled light signal with a photodetector based on coherent light scattered off of the anatomical scene and collected through the distal ends of the multimode optical fibers; and
   appending classifying data to the control speckled light signal indicative of one or more characteristics of the anatomical scene.

20. The non-transitory, machine-readable storage medium of claim 19, wherein training the machine learning classifier further comprises:

emitting second control coherent light from a second control coherent light source into the distal of the multimode optical fibers and onto the anatomical scene with the distal ends of the plurality of multimode optical fibers, wherein the second control coherent light source has a second emission spectrum different than an emission spectrum of the control coherent light source.

21. The endoscopic system of claim 1, the machine learning classifier is selected from the group consisting of a support vector machine (SVM), an artificial neural network, a Bayesian network, a random forest approach, a convolutional neural network, a deep neural network, and combinations thereof.

* * * * *